United States Patent
Adden et al.

(10) Patent No.: US 9,216,191 B2
(45) Date of Patent: Dec. 22, 2015

(54) METHODS AND COMPOSITION FOR INDUCING SATIETY

(71) Applicant: Dow Global Technologies LLC, Midland, MI (US)

(72) Inventors: Roland Adden, Walsrode (DE); Matthias Knarr, Nienburg/Weser (DE); Britta Huebner-Keese, Uetze (DE); Robert L. Sammler, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 15 days.

(21) Appl. No.: 14/350,819

(22) PCT Filed: Oct. 11, 2012

(86) PCT No.: PCT/US2012/059713
§ 371 (c)(1),
(2) Date: Apr. 10, 2014

(87) PCT Pub. No.: WO2013/059064
PCT Pub. Date: Apr. 25, 2013

(65) Prior Publication Data
US 2015/0045320 A1      Feb. 12, 2015

Related U.S. Application Data

(60) Provisional application No. 61/549,025, filed on Oct. 19, 2011.

(51) Int. Cl.
| | | |
|---|---|---|
| *A61K 31/717* | (2006.01) | |
| *A61K 31/7016* | (2006.01) | |
| *C08B 11/02* | (2006.01) | |
| *A61P 3/04* | (2006.01) | |
| *A23L 1/308* | (2006.01) | |
| *A23L 1/00* | (2006.01) | |
| *A23L 1/0534* | (2006.01) | |
| *A23L 1/09* | (2006.01) | |
| *A23L 1/29* | (2006.01) | |
| *A61K 31/7004* | (2006.01) | |
| *A61K 31/702* | (2006.01) | |

(52) U.S. Cl.
CPC ............ *A61K 31/717* (2013.01); *A23L 1/0017* (2013.01); *A23L 1/0534* (2013.01); *A23L 1/09* (2013.01); *A23L 1/293* (2013.01); *A23L 1/308* (2013.01); *A23L 1/3082* (2013.01); *A61K 31/702* (2013.01); *A61K 31/7004* (2013.01); *A61K 31/7016* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,042,719 A | 8/1977 | Zimmermann nee Ignacz et al. | |
| 4,316,982 A | 2/1982 | Holst et al. | |
| 5,582,351 A * | 12/1996 | Tsau | 241/17 |
| 6,235,893 B1 | 5/2001 | Reibert et al. | |
| 8,623,840 B2 | 1/2014 | Adden et al. | |
| 2011/0269711 A1 | 11/2011 | Adden | |

FOREIGN PATENT DOCUMENTS

| | | |
|---|---|---|
| DE | 10160409 A1 | 6/2003 |
| DE | 102010038644 A1 | 7/2011 |
| EP | 0210917 A2 | 4/1987 |
| EP | 1141029 B1 | 5/2003 |
| EP | 1423433 B1 | 6/2004 |
| FR | 2.218.882 | 9/1974 |
| WO | 92/09212 A1 | 6/1992 |
| WO | 2005/020718 A1 | 3/2005 |
| WO | 2005/020719 A1 | 3/2005 |
| WO | 2012/173838 A1 | 12/2012 |

OTHER PUBLICATIONS

Appetite, 51, 2008, p. 713-719, Paxman et al.
Abstract; Obesity, 19, 2011, p. 1171-1176, Peters et al.
Agr. Biol. Chem., 34, 1970, No. 12, p. 1867-1869, Naomichi et al, Effects of Sucrose and Citric Acid on the Sol-Gel Transformation of Methylcellulose in Water.
J. American Pharm. Assoc., 47, 1958, No. 1, p. 44-46, Levy et al, The Effect of Certain Additives on the Gel Point of Methylcellulose.
Carb. Research, 176, 1988, p. 137-144, Lindberg et al, Distribution of Substituents.
J. of Gas Chrom., 1964, p. 173-179, Ackman, Fundamental Groups in the Response of Flame Ionization Detectors to Oxygenated Aliphatic Hydrocarbons.
J. of Gas Chrom., 6, 1968, p. 135-138, Addison et al, Flame Ionization Detector Molar Responses for Methyl Esters of Some Polyfunctional Metabolic Acids.
Carb. Research, 40, 1975, p. 217-225, Sweet et al, Quantitative Analysis by various G.L.C. Response-Factor Theories for partially Ethylated Alditor Acetates.

\* cited by examiner

*Primary Examiner* — Leigh C Maier
(74) *Attorney, Agent, or Firm* — Beatrice Goldener

(57) ABSTRACT

A flowable or spoonable medicament, food, food ingredient or food supplement is useful for inducing satiety. It comprises (a) one or more mono-, di- and/or oligosaccharides and (b) a methylcellulose, wherein the methylcellulose has anhydroglucose units joined by 1-4 linkages wherein hydroxy groups of anhydroglucose units are substituted with methyl groups such that s23/s26 is from 0.17 to 0.36, wherein s23 is the molar fraction of anhydroglucose units wherein only the two hydroxy groups in the 2- and 3-positions of the anhydroglucose unit are substituted with methyl groups and wherein s26 is the molar fraction of anhydroglucose units wherein only the two hydroxy groups in the 2- and 6-positions of the anhydroglucose unit are substituted with methyl groups.

19 Claims, No Drawings

METHODS AND COMPOSITION FOR INDUCING SATIETY

The present invention relates to nutrition generally, and specifically to methods and compositions for inducing satiety.

In nutritional terms, satiety is a complex response, involving both an individual's emotional and physical perception of whether or not they have ingested enough. Satiety can be observed as a reduction of appetite immediately following consumption, or as a reduction of food intake at the next meal. For purposes of this specification, "satiety" refers to a net reduction of caloric intake, or a robust reduction in hunger responses, by an individual, and is often thought to arise at a sufficient gel fracture force $F_{GF}$ (37° C.).

As can be appreciated, control of satiety is most relevant in cases where an individual consumes more calories than are necessary. Inducing satiety can be useful for causing a reduced caloric intake, i.e., for aesthetic purposes (i.e., as a slimming aid for weight loss or weight management) or for medical treatment (for example, for treating obesity). Various strategies for inducing satiety have been developed.

WO 92/09212 discloses a dietary fiber composition comprising a water-soluble nonionic cellulose ether having a cloud point not greater than 35° C. and a charged surfactant at a weight ratio of surfactant to cellulose ether of 1/5 to 1/25. The composition is disclosed to be suitable for use as a slimming aid. The examples show that an ethyl hydroxyethyl cellulose having a cloud point of 34.4° C. gelled in water in combination with the ionic surfactant sodium dodecyl sulphate (SDS), but not in the absence of SDS. An ethyl hydroxyethyl cellulose having a cloud point of 35.9° C. and methylcellulose having a cloud point of 37° C. did not form a gel even in the presence of SDS and were not suitable.

WO 2005/020718 discloses a method for inducing satiety in a human or animal. The method comprises the step of administering to a human or animal an aqueous liquid or spoonable edible composition comprising at least 1% wt protein and from 0.1 to 5% wt of a biopolymer thickening agent which is not denatured or hydrolysed between pH 2 and 4. The edible composition having a gastric viscosity at a shear rate of 0.1 $s^{-1}$ and 37° C. of at least 20 Pa·s and the gastric viscosity is greater than the viscosity of the composition. WO 2005/020718 suggests a large number of biopolymers, such as ionic non-starch polysaccharides selected from alginates, pectins, carrageenans, amidated pectins, xanthans, gellans, furcellarans, karaya gum, rhamsan, welan, gum ghatti, and gum arabic. Of these, alginates are said to be especially preferred. Alternatively, neutral non-starch polysaccharides selected from galactamannan, guar gum, locust bean gum, tara gum, ispaghula, P-glucans, konjacglucomannan, methylcellulose, gum tragacanth, detarium, or tamarind may be used. Of these, galactamannan, guar gum, locust bean gum and tara gum are said to be especially preferred. The satiety effect of an alginate material that can be crosslinked with a co-administered calcium ion is shown in WO 2005/020718.

Unfortunately, skilled artisans have shown that a number of the biopolymer thickening agents listed in WO 2005/020718 do not induce satiety and, accordingly do not lead to a reduced caloric intake of individuals. R. Paxman, J. C. Richardson, P. W. Dettmar, B. M. Corfe "Daily ingestion of alginate reduces energy intake in free-living subjects", *Appetite* 51 (2008) 713-719, discuss a study conducted on normal-weight female volunteers which showed that following a preload of locust bean gum there was no difference in energy intake for the remainder of the day or the next day after a test meal when compared to a control. Dissonant outcomes in studies done with guar gum are also reported. J. R. Paxman et al. suggest the use of alginate and its ability to gel upon contact with multivalent cations. Sodium alginate can be cross-linked in the presence of either multivalent cations (ionic gelation) or through the formation of intra-molecular hydrogen bonds when the pH is lowered below 3.5 (acid gelation).

Harry P. F. Peters et al., "Dose-Dependent Suppression of Hunger by a Specific Alginate in a Low-Viscosity Drink Formulation", *Obesity* 19, 1171-1176 (June 2011) disclose that addition of specific types of alginates to drinks can enhance postmeal suppression of hunger, by forming strong gastric gels in the presence of calcium. Alginate drinks of 0.6 and 0.8% had an acceptable product viscosity (<0.5 Pa·s at 10 $s^{-1}$), provided gastric gel strength of 1.8 and 3.8 N respectively and produced a robust reduction in hunger responses.

However, the use of an alginate material that is crosslinked with a co-administered calcium ion is disadvantageous for several reasons. First, the calcium ion must be administered within a certain time of ingestion of the alginate in order to achieve gelation, thereby risking a complete lack of efficacy if the individual is delayed or distracted.

Second, the alginate material will only gel under certain pH conditions—thus, efficacy can be impaired or even destroyed by co-ingested foods or existing stomach contents.

Therefore, what is needed is a satiety inducing composition with a gelation mechanism that does not require a separate crosslinker, and that is not pH dependent.

One aspect of the present invention is a flowable or spoonable medicament, food, food ingredient or food supplement comprising (a) one or more mono-, di- and/or oligosaccharides and (b) a methylcellulose, wherein the methylcellulose has anhydroglucose units joined by 1-4 linkages wherein hydroxy groups of anhydroglucose units are substituted with methyl groups such that s23/s26 is from 0.17 to 0.36, wherein s23 is the molar fraction of anhydroglucose units wherein only the two hydroxy groups in the 2- and 3-positions of the anhydroglucose unit are substituted with methyl groups and wherein s26 is the molar fraction of anhydroglucose units wherein only the two hydroxy groups in the 2- and 6-positions of the anhydroglucose unit are substituted with methyl groups.

Another aspect of the present invention is a method for inducing satiety in an individual, which comprises administering to said individual the medicament, food, food ingredient or food supplement described above.

Yet another aspect of the present invention is a method for reversibly reducing stomach void volume in an individual, which comprises administering to said individual the medicament, food, food ingredient or food supplement described above.

Yet another aspect of the present invention is a method of reducing caloric intake in an individual, which comprises administering to said individual the medicament, food, food ingredient or food supplement described above.

The term "flowable or spoonable medicament, food, food ingredient or food supplement" as used herein means a medicament, food, food ingredient or food supplement that is flowable or spoonable at 10° C. and normal pressure.

The methylcellulose has anhydroglucose units joined by 1-4 linkages. Each anhydroglucose unit contains hydroxyl groups at the 2, 3, and 6 positions. Partial or complete substitution of these hydroxyls creates cellulose derivatives. For example, treatment of cellulosic fibers with caustic solution, followed by a methylating agent, yields cellulose ethers substituted with one or more methoxy groups. If not further substituted with other alkyls, this cellulose derivative is known as methylcellulose.

An essential feature of the flowable or spoonable medicament, food, food ingredient or food supplement of the present invention is a specific methylcellulose wherein hydroxy groups of anhydroglucose units are substituted with methyl groups such that s23/s26 is 0.36 or less, preferably 0.34 or less, more preferably 0.32 or less, most preferably 0.30 or less, and particularly 0.28 or less. Moreover, s23/s26 is 0.17 or more, preferably 0.18 or more, more preferably 0.19 or more, most preferably 0.20 or more and particularly 0.21 or more. One or more methylcelluloses, wherein s23/s26 is from 0.17 to 0.36, can be used in the medicament, food, food ingredient or food supplement of the present invention. In the case of more than one methylcellulose having such s23/s26 ratio, the weight ranges and weight ratios relating to methylcellulose relate to the total weight of all methylcelluloses wherein s23/s26 is from 0.17 to 0.36.

In the ratio s23/s26, s23 is the molar fraction of anhydroglucose units wherein only the two hydroxy groups in the 2- and 3-positions of the anhydroglucose unit are substituted with methyl groups and s26 is the molar fraction of anhydroglucose units wherein only the two hydroxy groups in the 2- and 6-positions of the anhydroglucose unit are substituted with methyl groups. For determining the s23, the term "the molar fraction of anhydroglucose units wherein only the two hydroxy groups in the 2- and 3-positions of the anhydroglucose unit are substituted with methyl groups" means that the two hydroxy groups in the 2- and 3-positions are substituted with methyl groups and the 6-positions are unsubstituted hydroxy groups. For determining the s26, the term "the molar fraction of anhydroglucose units wherein only the two hydroxy groups in the 2- and 6-positions of the anhydroglucose unit are substituted with methyl groups" means that the two hydroxy groups in the 2- and 6-positions are substituted with methyl groups and the 3-positions are unsubstituted hydroxy groups.

Formula I below illustrates the numbering of the hydroxy groups in anhydroglucose units.

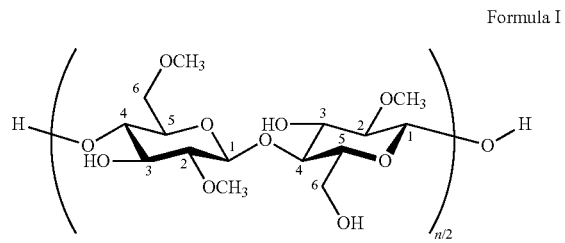

Formula I

The methylcellulose preferably has a DS(methyl) of from 1.55 to 2.25, more preferably from 1.65 to 2.20, and most preferably from 1.70 to 2.10. The degree of the methyl substitution, DS(methyl), also designated as DS(methoxyl), of a methylcellulose is the average number of OH groups substituted with methyl groups per anhydroglucose unit.

The determination of the % methoxyl in methylcellulose is carried out according to the United States Pharmacopeia (USP 34). The values obtained are % methoxyl. These are subsequently converted into degree of substitution (DS) for methyl substituents. Residual amounts of salt have been taken into account in the conversion.

The viscosity of the methylcellulose is preferably at least 50 mPa·s, more preferably at least 200 mPa·s, and most preferably at least 400 mPa·s, when measured as a 2 wt.-% aqueous solution at 5° C. at a shear rate of 10 s$^{-1}$. The viscosity of the methylcellulose is preferably up to 30000 mPa·s, more preferably up to 10000 mPa·s, and most preferably up to 7000 mPa·s, when measured as indicated above.

Conventionally, methylcellulose has been found to be very useful in a variety of applications, providing thickening, freeze/thaw stability, lubricity, moisture retention and release, film formation, texture, consistency, shape retention, emulsification, binding, gelation, and suspension properties. However, conventional methylcellulose does not form a sufficiently strong gel at temperatures as low as an individual's normal body temperature as shown in the accompanying examples. A conventional methylcellulose that does not form a sufficiently strong gel does not reduce stomach void volume in an individual and accordingly does not induce satiety to result in a sufficient reduction of energy intake.

One unusual property of methylcellulose is that it is known to exhibit reverse thermal gelation in water; in other words, methylcellulose gels at warmer temperatures and forms a liquid at cooler temperatures. Most grades of methylcellulose, dissolved in water of about 5° C. at 2 wt. %, will gel at least about 10° C. higher than the normal body temperature of a human being. A grade of methylcellulose that gels at a relatively low temperature, 38° C. to 44° C., is generally available under the tradename METHOCEL SG or SGA (The Dow Chemical Company). No grades of commercially available methylcellulose gel at temperatures as low as an individual's normal body temperature; however, U.S. Pat. No. 6,235,893, the entirety of which is incorporated by reference herein, teaches the preparation of methylcelluloses that gel as low as 31° C.

It has been suggested by skilled artisans that addition of specific types of compounds to food can enhance suppression of hunger when the compounds form strong gastric gels after consumption of the drinks. Strong gels can be formed at a temperature of an individual's normal body temperature by including in food high concentrations, e.g, concentrations of 5 weight percent or more, of a gelling methylcellulose, but high concentrations of the methylcellulose described above are not accepted by many consumers for organoleptic reasons, specifically the slightly slimy texture when the methylcellulose described above is incorporated in food at high concentrations.

In vitro gel fracture force of the gelled liquid having a temperature of 37° C. is a proxy for in vivo gelling. Surprisingly, it has been found that the gel fracture force of an aqueous gelled composition can be increased without substantially increasing the concentration of the methylcellulose in the composition by combining the methylcellulose described above with one or more mono-, di- and/or oligosaccharides. When the concentration of the methylcellulose described above is kept constant, the presence of one or more mono-, di- and/or oligosaccharides enables the production of compositions, such as liquids, which exhibit an increased gel strength (determined as gel fracture force) when the aqueous composition reaches the normal body temperature of an individual. Alternatively, the concentration of the methylcellulose described above in a composition, such as a liquid, can be decreased while still maintaining a sufficiently high gel strength at the temperature of an individual's normal body temperature.

It has also been found that the presence of one or more mono-, di- and/or oligosaccharides in a 2 wt. % aqueous solution of the above described methylcellulose can decrease the gelation temperature of the methylcellulose to 30° C. or less, often even to 25° C. or less, and in some embodiments even to 22° C. or less.

It is known that the incorporation of sucrose in aqueous solutions of methylcellulose decreases the gelation temperature of the methylcellulose in the aqueous solution, see for example N. Iso et al, Effects of Sucrose and Citric Acid on the Sol-Gel Transformation of Methylcellulose in Water, *Agr. Biol. Chem.*, Vol. 34, No. 12, p. 1867-1869, 1970; and G. Levy et al., The Effect of Certain Additives on the Gel Point of Methylcellulose, *Journal of the American Pharmaceutical Association* p. 44-46, January 1958. For example, 20% sucrose in a 2 wt. % aqueous solution of the commercially available METHOCEL A15C methylcellulose decreases the gelation temperature from 50 to 44° C. (see METHOCEL Cellulose Ethers Technical Handbook, published September 2002 by The Dow Chemical Company). However, it is highly surprising that by the present invention a gelation temperature of 30° C. or less, in many embodiments of the invention a gelation temperature of even 25° C. or less and in some embodiments a gelation temperature of even 22° C. or less can be achieved.

Accordingly, one or more mono-, di- and/or oligosaccharides are another essential feature of the flowable or spoonable medicament, food, food ingredient or food supplement of the present invention. Useful monosaccharides have the elemental chemical formula $C_xH_{2x}O_x$, where x is at least 3, preferably from 3 to 7, more preferably 4, 5 or 6, and most preferably 6. Preferred monosaccharides are glucose and fructose. Useful disaccharides are, for example, lactose, maltose and sucrose. Sucrose, commonly also designated as saccharose, is preferred. Oligosaccharides have 3 to 10, preferably 3 to 7, monosaccharide units linked by glycosidic bonds. Examples of oligosaccharides are fructo-oligosaccharides, such as fructans, or galacto-oligosaccharides, or manno-oligosaccharides, or galactomanno-oligosaccharides, or gluco-oligosaccharides, such as maltodextrins or cyclodextrins or cellodextrins. The flowable or spoonable medicament, food, food ingredient or food supplement of the present invention can comprise more than one type of mono-, di- and/or oligosaccharides as component (a). The weight ranges and weight ratios relating to component (a) relates to the total weight of the mono-, di- and/or disaccharides. Preferred examples of component (a) are listed in the Council Directive 2001/111/EC of 20 Dec. 2001 relating to certain sugars intended for human consumption, as published in the Official Journal of the European Communities L 10/53, 12.1.2002, such as semi-white sugar, (white) sugar, dried glucose syrup, dextrose, dextrose monohydrate, anhydrous dextrose or fructose. These sugars can be in solid or liquid form. Council Directive 2001/111/EC lists sugar solution, invert sugar solution, invert sugar syrup or glucose syrup. The sugar solution, invert sugar solution and invert sugar syrup are characterized by dry matter of not less than 62% by weight.

The weight ratio w(a)/w(b), i.e., the weight ratio of (a) the total of one or more mono-, di- and/or oligosaccharides and (b) the methylcellulose, preferably is at least 1.0/1.0, more preferably at least 2.0/1.0, most preferably at least 3.5/1.0, and particularly at least 5.0/1.0. The weight ratio weight ratio w(a)/w(b) is preferably up to 40:1.0, more preferably up to 30:1.0, most preferably up to 20:1.0, and particularly up to 15:1.0.

When the medicament, food, food ingredient or food supplement is in powder or granular form, the amount of the sum of (a) one or more mono-, di- and/or oligosaccharides and (b) one or more methylcelluloses as described above, wherein s23/s26 is from 0.17 to 0.36, is preferably from 10 to 100 weight percent, more preferably from 40 to 100 weight percent, and most preferably from 75 to 98 weight percent, based on the total weight of the dry composition. Without wanting to be bound to the theory, applicants believe that the medicament, food, food ingredient or food supplement of the present invention generally forms a gel mass in the individual's stomach when the medicament, food, food ingredient or food supplement is ingested by an individual.

It is contemplated that, in one embodiment, the medicament, food, food ingredient or food supplement is useful for indications that require gastric volume to be occupied for at least 60 minutes, preferably at least 120 minutes, more preferably at least 180 minutes, and most preferably at least 240 minutes.

In another embodiment, the medicament is useful for treating gastric ulcers, gastro-esophageal reflux disease, or obesity. In a preferred embodiment, the medicament is useful for treating obesity.

Alternatively, in another embodiment, the food, food ingredient or food supplement is useful as a slimming aid, weight loss aid, or weight control aid in a non-obese individual, for example for aesthetic reasons.

Alternatively, in another embodiment, the food supplement is useful for reducing total daily caloric intake.

In another embodiment, the present invention provides a method for inducing satiety or for reversibly reducing stomach void volume in an individual, comprising administering to said individual the above described methylcellulose and one or more mono-, di- and/or oligosaccharides in the above-described weight ratio, which combination gels in the individual's stomach.

The flowable or spoonable medicament, food, food ingredient or food supplement can be in powder or granular form designed to be mixed with an aqueous liquid before consumption. The powder or granular form is flowable. Alternatively, the flowable or spoonable medicament, food, food ingredient or food supplement additionally comprises an aqueous liquid.

When the medicament, food, food ingredient or food supplement comprises an aqueous liquid or when the medicament, food, food ingredient or food supplement in powder or granular form is mixed with an aqueous liquid before consumption, the amount of the aqueous liquid is advantageously chosen that the amount of the methylcellulose is from 0.5 to 2.5 weight percent, preferably from 0.7 to 2.3 weight percent, more preferably from 1.0 to 2.2 weight percent, and most preferably from 1.2 to 2.1 weight percent, based on the total weight of the liquid composition. The amount of component (a), i.e., the total amount of one or more mono-, di- and/or oligosaccharides, preferably is from 2.0 to 40 weight percent, more preferably from 5.0 to 30 weight percent, most preferably from 7.5 to 25 weight percent, and particularly from 10 to 20 weight percent, based on the total weight of the liquid composition. The remaining portions are optional ingredients as described further below and liquid, such as water.

Preferably, the combination of methylcellulose and mono-, di- and/or oligosaccharides enters the stomach in liquid form. For purposes of this specification, "liquid" refers to any substance that takes the shape of its container at 10° C.

Non-limiting examples of the flowable or spoonable medicament, food, food ingredient or food supplement of the present invention include yogurts, smoothies, drinks, shakes, fruit beverages, beverage shots, sports drinks, and other solutions, as well as emulsions, including ice creams, creams, mousses, cream cheese, ketchup, spreads, dips, picante, salad dressing, homogenized milk, mayonnaise, gravies, puddings, soups, sauces, sport drinks and breakfast type cereal products such as porridge. The spoonable medicament, food, food ingredient or food supplement of the present invention can comprise one or more mono-, di- and/or oligosaccharides from a natural source, but in this case the amount of these mono-, di- and/or oligosaccharides should be taken into account for determining the preferred weight ratio of (a) mono-, di- and/or oligosaccharides to (b) methylcellulose and the preferred weight ranges of mono-, di- and/or oligosaccharides to be incorporated in the medicament, food, food ingredient or food supplement.

Preferably the medicament, food, food ingredient or food supplement is a meal replacer or other food product intended to be used in a weight loss or weight control plan.

The present invention provides an effective and convenient method of providing good satiety effects to food compositions, especially those intended to be used in a weight loss or weight control plan. Furthermore, the products can be manufactured by conventional techniques and are economical to produce. They are also stable upon storage below 10° C.

Flavoring agents may be added to the medicament, food, food ingredient or food supplement, including varying types of cocoa, pure vanilla or artificial flavour, such as vanillin, ethyl vanillin, chocolate, malt, and mint, extracts or spices, such as cinnamon, nutmeg and ginger, and mixtures thereof. The edible compositions may comprise one or more conventional colourants, in conventional amounts as desired. The medicament, food, food ingredient or food supplement may comprise additional ingredients, such as added vitamins, added minerals, herbs, flavoring agents, antioxidants, preservatives or mixtures thereof.

For a human, the individual should generally consume at least two, preferably at least three grams of methylcellulose. However, not to be bound by any theory it is believed that the gel fracture force, (i.e., the gel strength) and volume of the gel mass in vivo are the primary considerations. Administration of a 300 mL volume of liquid of a 2% solution, a 1.5% solution, and even a 1.0% solution are contemplated. Alternatively administration of a 2% solution in a 200 mL volume is possible.

In one embodiment, the individual should abstain from imbibing further liquids until the combination of methylcellulose and one or more mono-, di- and/or oligosaccharides has an opportunity to gel.

In one embodiment, the combination of methylcellulose and one or more mono-, di- and/or oligosaccharides substantially gels in at least 45 minutes, preferably in at least 20 minutes, and more preferably, in at least 15 minutes, upon entering the stomach. When the combination of the methylcellulose and one or more mono-, di- and/or oligosaccharides are ingested by an individual, the combination of the methylcellulose, one or more mono- and/or disaccharides, and water forms a gel mass in the individual's stomach.

In vitro gel fracture force $F_{GF}$ (37° C.) of the aqueous gelled composition having a temperature of 37° C. is a proxy for in vivo gelling. An $F_{GF}$ (37° C.) of at least 1.5 N is preferred, more preferably at least 1.8 N, most preferably at least 2.0 N, and particularly at least 2.2 N. In one embodiment, one or more mono-, di- and/or oligosaccharides are combined with the methylcellulose in the flowable or spoonable medicament, food, food ingredient or food supplement of the present invention in such a weight ratio that the $F_{GF}$ (37° C.) is increased by generally more than 50 percent, preferably at least 100 percent, more preferably at least 150 percent, and particularly at least 200 percent, as compared to a $F_{GF}$ (37° C.) obtained by gelling a comparable flowable or spoonable medicament, food, food ingredient or food supplement that does not comprise a mono-, di- and/or disaccharide.

In a preferred embodiment, the gelation is temperature-activated by the individual's body temperature, and no crosslinker is required.

In yet another embodiment, the present invention provides a method for reversibly reducing stomach void volume in an individual, comprising administering to said individual the above-described medicament, food, food ingredient or food supplement that comprises the above-mentioned methylcellulose that gels in the individual's stomach. Not to be bound by any theory, formation of the gel mass causes distention of the stomach wall to occur resulting in a biological signal of satiety and leaving less of the individual's stomach volume available for food. In a preferred embodiment, the above-described medicament, food, food ingredient or food supplement comprising the above-mentioned methylcellulose has a gel temperature below that of the individual's body temperature.

In yet another embodiment, the present invention provides a method of reducing caloric intake in an individual, comprising administering to said individual, a liquid comprising the above-described methylcellulose that gels in the individual's stomach. In this embodiment, the combination of methylcellulose and one or more mono-, di- and/or oligosaccharides is preferably administered at least 45 minutes, more preferably at least 20 minutes, and most preferably, at least 15 minutes, before the individual eats. The combination of methylcellulose and one or more mono-, di- and/or oligosaccharides is preferably administered up to 6 hours, more preferably up to 4 hours, and most preferably, up to 2 hours, before the individual eats.

It is understood that the individual's stomach eventually breaks down the gel mass, allowing it to pass from the stomach into the upper gastrointestinal tract. Naturally occurring mechanisms that break down the gel mass include physical disruption by stomach mobility and dilution with gastric juices (and consequent reversion to a liquid form). Degradation of gel mass occurs generally within 2 hours, preferably within 4 hours, and more preferably within 6 hours.

Methods of making methylcellulose are described in more detail in the Examples. Generally, cellulose pulp is treated with a caustic, for example an alkali metal hydroxide. Preferably, about 1.5 to about 3.0 mol NaOH per mol of anhydroglucose units in the cellulose is used. Uniform swelling and alkali distribution in the pulp is optionally controlled by mixing and agitation. The rate of addition of aqueous alkaline hydroxide is governed by the ability to cool the reactor during the exothermic alkalization reaction. In one embodiment, an organic solvent such as dimethyl ether is added to the reactor as a diluent and a coolant. Likewise, the headspace of the reactor is optionally purged with an inert gas (such as nitrogen) to minimize unwanted reactions with oxygen and molecular weight losses of the methylcellulose. In one embodiment, the temperature is maintained at or below 45° C. In one embodiment, the temperature is maintained at or below about 45° C.

A methylating agent, such as methyl chloride, is also added by conventional means to the cellulose pulp, either before, after, or concurrent with the caustic, generally in an amount of 2.0 to 3.5 mol methylating agent per mol of anhydroglucose units in the cellulose. Preferably, the methylating agent is added after the caustic. Once the cellulose has been contacted with caustic and methylating agent, the reaction temperature is increased to about 75° C. and reacted at this temperature for about half an hour.

In a preferred embodiment, a staged addition is used, i.e., a second amount of caustic is added to the mixture over at least 30 minutes, preferably at least 45 minutes, while maintaining the temperature at 20 to 70° C. Preferably, 2 to 4 mol caustic per mol of anhydroglucose units in the cellulose is used. A staged second amount of methylating agent is added to the mixture, either before, after, or concurrent with the caustic, generally in an amount of 2 to 4.5 mol methylating agent per mol of anhydroglucose units in the cellulose. Preferably, the second amount of methylating agent is added prior to the second amount of caustic.

The methylcellulose is washed to remove salt and other reaction by-products. Any solvent in which salt is soluble may be employed, but water is preferred. The methylcellulose may be washed in the reactor, but is preferably washed in a separate washer located downstream of the reactor. Before or after washing, the methylcellulose may be stripped by exposure to steam to reduce residual organic content. The cellulose ether may subsequently be subjected to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent.

The methylcellulose is dried to a reduced moisture and volatile content of preferably 0.5 to 10.0 weight percent water and more preferably 0.8 to 5.0 weight percent water and volatile based upon the weight of methylcellulose. The reduced moisture and volatiles content enables the methylcellulose to be milled into particulate form. The methylcellulose is milled to particulates of desired size. If desired, drying and milling may be carried out simultaneously.

EXAMPLES

The following examples are for illustrative purposes only and are not intended to limit the scope of the present invention.

Unless otherwise mentioned, all parts and percentages are by weight. In the Examples the following test procedures are used.

Production of Methylcellulose 1 (MC-1)

Finely ground wood cellulose pulp is loaded into a jacketed, agitated reactor. The reactor is evacuated and purged with nitrogen to remove oxygen and then evacuated again. The reaction is carried out in two stages. In the first stage a 50 weight percent aqueous solution of sodium hydroxide is sprayed onto the cellulose until the level reaches 2.5 mol of sodium hydroxide per mol of anhydroglucose units in the cellulose, and then the temperature is adjusted to 35° C. After stirring the mixture of aqueous sodium hydroxide solution and cellulose for about 10 minutes at 35° C., 0.9 mol of dimethyl ether and 3.1 mol of methyl chloride per mol of anhydroglucose units are added to the reactor. The contents of the reactor are then heated in 85 min to 80° C. After having reached 80° C., the first stage reaction is allowed to proceed for 5 min. Then the reaction is cooled down to 60° C. in 20 min.

The second stage of the reaction is started by addition of a 50 weight percent aqueous solution of sodium hydroxide at an amount of 0.7 mol of sodium hydroxide per mol of anhydroglucose units. The addition time for the sodium hydroxide solution is 30 min. Then methyl chloride at an amount of 1.8 mol of methyl chloride per mol of anhydroglucose units is added over a time period of 45 min After the reaction, the reactor is vented. The contents of the reactor are removed and transferred to a tank containing hot water. The crude methylcellulose is then washed with hot water and dried in an air-swept drier. The material is then ground in a mill with a 0.6 mm screen.

The methylcellulose is partially depolymerized by contacting it with 1.1 g of gaseous HCl per kg of methylcellulose at a temperature of 50° C. during 240 minutes and subsequently neutralized with sodium bicarbonate.

Production of Methylcelluloses 2-6 (MC-2 to MC-6)

Methylcelluloses 2-6 are produced according to the following procedure. Finely ground wood cellulose pulp is loaded into a jacketed, agitated reactor. The reactor is evacuated and purged with nitrogen to remove oxygen, and then evacuated again. The reaction is carried out in two stages. In the first stage, a 50 weight percent aqueous solution of sodium hydroxide is sprayed onto the cellulose until the level reaches 1.8 mol of sodium hydroxide per mol of anhydroglucose units of the cellulose, and then the temperature is adjusted to 40° C. After stirring the mixture of aqueous sodium hydroxide solution and cellulose for about 20 minutes at 40° C., 1.5 mol of dimethyl ether and 2.3 mol of methyl chloride per mol of anhydroglucose units are added to the reactor. The contents of the reactor are then heated in 60 min to 80° C. After having reached 80° C., the first stage reaction is allowed to proceed for 5 min. Then the reaction is cooled down to 40° C. within about 30 min.

The second stage of the reaction is started by addition of methyl chloride in an amount of 3.4 molar equivalents of methyl chloride per mol of anhydroglucose units. The addition time for methyl chloride is 20 min. Then a 50 weight percent aqueous solution of sodium hydroxide at an amount of 2.9 mol of sodium hydroxide per mol of anhydroglucose units is added over a time period of 90 min. The rate of addition is 0.032 mol of sodium hydroxide per mol of anhydroglucose units per minute. After the second stage addition is completed, the contents of the reactor are heated up to 80° C. in 20 min and then kept at a temperature of 80° C. for 120 min.

After the reaction, the reactor is vented and cooled down to about 50° C. The contents of the reactor are removed and transferred to a tank containing hot water. The crude methylcellulose is then neutralized with formic acid and washed chloride free with hot water (assessed by $AgNO_3$ flocculation test), cooled to room temperature and dried at 55° C. in an air-swept drier. The material is then ground using e.g. an Alpine UPZ mill using a 0.5-mm screen.

The methylcellulose is partially depolymerized by contacting it with 3 g of gaseous HCl per kg of methylcellulose at a temperature of 55-70° C. during 10-30 minutes and subsequently neutralized with sodium bicarbonate. The exact temperature and time period is adjusted to the viscosity to be achieved by series trials. A skilled artisan knows how to adjust the depolymerization temperature and time period to the desired viscosity.

Production of Methylcelluloses 7-9 (MC-7 to MC-9)

The methylcelluloses 7-9 are produced in the same manner as methylcelluloses 2-6, except that during the reaction of the methylcellulose the conditions as shown in Table 1 have been used. The partial depolymerization temperature and time period have been adjusted to achieve the viscosities as listed in Table 3.

TABLE 1

| Methylcellulose production | | | |
|---|---|---|---|
| Methylcellulose (MC) | 7 | 8 | 9 |
| Time period of addition of sodium hydroxide of a second stage [min] | 45 | 45 | 90 |
| Temperature of addition of sodium hydroxide of a second stage [° C.] | 50 | 50 | 80 |

The properties of the methylcelluloses 1-10 are measured as described below. Their properties are listed in Table 3 below.

Production of a 2% Aqueous Solution of the Methylcellulose

To obtain a 2% aqueous solution of methylcellulose, 3 g of milled, ground, and dried methylcellulose (under consideration of the water content of the methylcellulose) were added to 147 g of tap water (temperature 20-25° C.) at room temperature while stirring with an overhead lab stirrer at 750 rpm with a 3-wing (wing=2 cm) blade stirrer. The solution was then cooled to 1.5° C. After the temperature of 1.5° C. was reached the solution was stirred for 180 min at 750 rpm. Prior to use or analysis, the solution was stirred for 15 min at 100 rpm in an ice bath.

Production of a Solution of the Methylcellulose and a Mono- or Disaccharide

To obtain an aqueous solution of methylcellulose and a mono- or disaccharide, the dry powder of the mono- or disaccharide (dry mass larger than 95%) was added to tap water (temperature 20-25° C.) at room temperature while stirring with an overhead lab stirrer at 750 rpm with a 3-wing (wing=2 cm) blade stirrer. The solution was stirred for 5 min at 750 rpm, then the dry powder of methylcellulose (milled, ground, and dried, under consideration of the water content of the methylcellulose) was added to the solution of the mono- or disaccharide (temperature 20-25° C.) at room temperature while still stirring with an overhead lab stirrer at 750 rpm with a 3-wing (wing=2 cm) blade stirrer. The solution was then cooled to about 1.5° C. After the temperature of 1.5° C. was reached the solution was stirred for 180 min at 750 rpm. The total amounts can be calculated based on the weight percent of methylcellulose and mono- or disaccharide as given in Table 4 further below.

Production of a Smoothie Comprising Methylcellulose

The smoothie is an apple/banana juice which is commercially available from Voelkel, Germany. It has the composition as listed in Table 2 below.

TABLE 2

Composition of Smoothie

| Components | Unit | "Voelkel" Apple-Banana juice | Test Method |
|---|---|---|---|
| Total dry weight | [%] | 15.3 | BVL L 31.00-18 |
| Ash | [%] | 0.35 | BVL L 31.00-4 |
| titratable acid | [mmol/kg] | 59.2 | BVL L 31.00-3 |
| Water-insoluble solids | [%] | 0.54 | ISO 751 |
| D-Glucose | [%] | 3.01 | BVL L 31.00-12 |
| D-Fructose | [%] | 5.39 | BVL L 31.00-12 |
| Saccharose | [%] | 3.74 | BVL L 31.00-13 |

The methylcellulose was dissolved in the smoothie by addition of the dry powder of methylcellulose (milled, ground, and dried, under consideration of the water content of the methylcellulose) to the smoothie (temperature 20-25° C.) at room temperature while stirring with an overhead lab stirrer at 750 rpm with a 3-wing (wing=2 cm) blade stirrer. The smoothie was then cooled to about 1.5° C. After the temperature of 1.5° C. was reached the smoothie was stirred for 180 min at 750 rpm. The total amounts can be calculated based on the weight percent of methylcellulose as given in Table 4 further below.

Determination of the DS(Methyl) of Methylcellulose

The determination of the % methoxyl in methylcellulose was carried out according to the United States Pharmacopeia (USP34). The values obtained were % methoxyl. These were subsequently converted into degree of substitution (DS) for methyl substituents. Residual amounts of salt were taken into account in the conversion.

Determination of the Gelation Temperature of Aqueous Methylcellulose

Aqueous methylcellulose solutions were subjected to small-amplitude oscillatory shear flow (frequency=2 Hz, strain amplitude=0.5%) while warming from 5 to 85° C. at 1 K/min in a rotational rheometer (Anton Paar, MCR 501, Peltier temperature-control system). The oscillatory shear flow was applied to the sample placed between parallel-plate fixtures (type PP-50; 50-mm diameter, 1-mm separation [gap]). Water loss to the sheared material was minimized during the temperature ramp by (1) covering the fixtures with a metal ring (inner diameter of 65 mm, width of 5 mm, height of 15 mm) and (2) placing a water-immiscible paraffin oil around the sample perimeter. The storage modulus G', which is obtained from the oscillation measurements, represents the elastic properties of the solution (during the gelation process of methylcellulose, G' increases). The loss modulus G", which is obtained from the oscillation measurements, represents the viscous properties of the solution. The gelation temperature, $T_{gel}$, is identified as the temperature when G' and G" are equal (e.g. $T_{gel}$=T(G'=G")).

Determination of the Viscosity of Aqueous Methylcellulose

The steady-shear-flow viscosities η (5° C., 10 s$^{-1}$, 2 wt. % MC) of aqueous 2-wt. % methylcellulose solutions were measured at 5° C. at a shear rate of 10 s$^{-1}$ with an Anton Paar Physica MCR 501 rheometer and cone-and-plate sample fixtures (CP-50/1, 50-mm diameters).

Determination of the Viscosity of Aqueous Solutions of Methylcellulose and Mono- or Disaccharide The steady-shear-flow viscosity η (5° C., 10 s$^{-1}$) of mixtures of methylcellulose and mono- or disaccharide dissolved in water were measured at 5° C. at a shear rate of 10 s$^{-1}$ using an Haake RS1 rheometer with cone-and-plate sample fixtures (CP-60/1, 60-mm-diameter).

Determination of the Gel Fracture Force $F_{GF}$ (37° C.)

Cylindrically-shaped gels (height=20 mm, diameter=20 mm) were fabricated by introducing about 6.5 g of an aqueous formulation having a temperature of about 5° C. into a syringe (20-mL volume, NORM-JECT Luer, one end cut off above the needle port), sealing the cut end with glass, and placing the syringe in a constant-temperature water bath (set at 39.5° C.) for one hour.

The gel fracture force $F_{GF}$ (37° C.) was measured with a Texture Analyzer (model TA.XTPlus; Stable Micro Systems, 5-Kg load cell) located inside a cabinet (model XT/TCH Stable Micro Systems, Surrey, UK) designed to hold the temperature at 37.0° C. The cylindrically-shaped gels were compressed between two plates (50-mm-diameter, plate compression rate=10 mm/s, trigger force=0.5 g, maximum distance=18 mm) within about two to three minutes after removal from the 39.5° C. water bath. The plate displacement [mm] and compression force [N] was measured at selected time intervals (400 points/s) until the gel collapses. The maximum compressional force, measured prior to the gel collapse, is identified as $F_{GF}$ (37° C.). The results of six replicates were typically averaged and the average results reported in units of Newton (e.g. see the data in Table 4).

Determination of s23/s26 of Methylcellulose

The approach to measure the ether substituents in methylcellulose is generally known. See for example the approach described in principle for Ethyl Hydroxyethyl Cellulose in Carbohydrate Research, 176 (1988) 137-144, Elsevier Science Publishers B.V., Amsterdam, DISTRIBUTION OF SUBSTITUENTS IN O-ETHYL-O-(2-HYDROXY-ETHYL)CELLULOSE by Bengt Lindberg, Ulf Lindquist, and Olle Stenberg.

Specifically, determination of s23/s26 was conducted as follows: 10-12 mg of the methylcellulose were dissolved in 4.0 mL of dry analytical-grade dimethyl sulfoxide (DMSO) (Merck, Darmstadt, Germany, stored over 0.3 nm molecular sieve beads) at about 90° C. with stirring and then cooled to room temperature. The solution was stirred at room temperature over night to ensure complete solubilization/dissolution. The entire perethylation including the solubilization of the methylcellulose was performed using a dry nitrogen atmosphere in a 4 mL screw cap vial. After solubilization, the dissolved methylcellulose was transferred to a 22-mL screw-cap vial to begin the perethylation process. Powdered sodium hydroxide (freshly pestled, analytical grade, Merck, Darmstadt, Germany) and ethyl iodide (for synthesis, stabilized with silver, Merck-Schuchardt, Hohenbrunn, Germany) were introduced in a thirty-fold molar excess relative to the level of anhydroglucose units in the methylcellulose, and the mixture was vigorously stirred under nitrogen in the dark for three days at ambient temperature. The perethylation was repeated with addition of the threefold amount of the reagents sodium hydroxide and ethyl iodide compared to the first reagent addition, and stirring at room temperature was continued for an additional two days. Optionally, the reaction mixture could be diluted with up to 1.5 mL DMSO to ensure good mixing during the course of the reaction. Next, five mL of 5% aqueous sodium thiosulfate solution was poured into the reaction mixture, and the mixture was then extracted three times with 4 mL of dichloromethane. The combined extracts were washed three times with 2 mL of water. The organic phase was dried with anhydrous sodium sulfate (about 1 g). After filtration, the solvent was removed with a gentle stream of nitrogen, and the sample was stored at 4° C. until needed.

Hydrolysis of about 5 mg of the perethylated samples was performed under nitrogen in a 2-mL screw-cap vial with 1 mL of 90% aqueous formic acid under stirring at 100° C. for 1 hour. The acid was removed in a stream of nitrogen at 35-40° C. and the hydrolysis was repeated with 1 mL of 2M aqueous trifluoroacetic acid for 3 hours at 120° C. in an inert nitrogen atmosphere with stirring. After completion, the acid was removed to dryness in a stream of nitrogen at ambient temperature using ca. 1 mL of toluene for co-distillation.

The residues of the hydrolysis were reduced with 0.5 mL of 0.5-M sodium borodeuteride in 2N aqueous ammonia solution (freshly prepared) for 3 hours at room temperature with stirring. The excess reagent was destroyed by dropwise addition of about 200 µL of concentrated acetic acid. The resulting solution is evaporated to dryness in a stream of nitrogen at about 35-40° C. and subsequently dried in vacuum for 15 min at room temperature. The viscous residue was dissolved in 0.5 mL of 15% acetic acid in methanol and evaporated to dryness at room temperature. This was done five times and repeated four additional times with pure methanol. After the final evaporation, the sample was dried in vacuum overnight at room temperature.

The residue of the reduction was acetylated with 600 µL of acetic anhydride and 150 µL of pyridine for 3 hrs at 90° C. After cooling, the sample vial was filled with toluene and evaporated to dryness in a stream of nitrogen at room temperature. The residue was dissolved in 4 mL of dichloromethane and poured into 2 mL of water and extracted with 2 mL of dichloromethane. The extraction was repeated three times. The combined extracts were washed three times with 4 mL of water and dried with anhydrous sodium sulfate. The dried dichloromethane extract was subsequently submitted to GC analysis. Depending on the sensitivity of the GC system, a further dilution of the extract could be necessary.

Gas-liquid (GLC) chromatographic analyses were performed with Agilent 6890N type of gas chromatographs (Agilent Technologies GmbH, 71034 Boeblingen, Germany) equipped with Agilent J&W capillary columns (30 m, 0.25-mm ID, 0.25-µm phase layer thickness) operated with 1.5-bar helium carrier gas. The gas chromatograph was programmed with a temperature profile that held constant at 60° C. for 1 min, heated up at a rate of 20° C./min to 200° C., heated further up with a rate of 4° C./min to 250° C., and heated further up with a rate of 20° C./min to 310° C. where it is held constant for another 10 min. The injector temperature is set to 280° C. and the temperature of the flame ionization detector (FID) was set to 300° C. Exactly 1 µL of each sample is injected in the splitless mode at 0.5-min valve time. Data are acquired and processed with a LabSystems Atlas work station.

Quantitative monomer composition data are obtained from the peak areas measured by GLC with FID detection. Molar responses of the monomers are calculated in line with the effective carbon number (ECN) concept but modified as described in the table below. The effective carbon number (ECN) concept has been described by Ackman (R. G. Ackman, J. Gas Chromatogr., 2 (1964) 173-179 and R. F. Addison, R. G. Ackman, J. Gas Chromatogr., 6 (1968) 135-138) and applied to the quantitative analysis of partially alkylated alditol acetates by Sweet et. al (D. P. Sweet, R. H. Shapiro, P. Albersheim, Carbohyd. Res., 40 (1975) 217-225).

ECN Increments Used for ECN Calculations:

| Type of carbon atom | ECN increment |
|---|---|
| hydrocarbon | 100 |
| primary alcohol | 55 |
| secondary alcohol | 45 |

In order to correct for the different molar responses of the monomers, the peak areas were multiplied by molar response factors MRFmonomer which are defined as the response relative to the 2,3,6-Me monomer. The 2,3,6-Me monomer were chosen as reference since it was present in all samples analyzed in the determination of s23/s26.

MRFmonomer=ECN2,3,6-Me/ECNmonomer

The mol fractions of the monomers were calculated by dividing the corrected peak areas by the total corrected peak area according to the following formulas:

(1) s23 is the sum of the molar fractions of anhydroglucose units which meet the following condition [the two hydroxy groups in the 2- and 3-positions of the anhydroglucose unit are substituted with methyl groups, and the 6-position is not substituted (=23-Me)]; and (2) s26 is the sum of the molar fractions of anhydroglucose units which meet the following condition [the two hydroxy groups in the 2- and 6-positions of the anhydroglucose unit are substituted with methyl groups, and the 3-position is not substituted (=26-Me)].

Key chemical structural parameters and properties of ten methylcellulose materials are listed in Table 3 below. The mean values±two standard deviations (2σ) of the mol fraction (26-Me), the mol fraction (23-Me) and s23/s26 are listed.

Eight materials are MC-1 to MC-8 with an s23/s26 ratio of from 0.17 to 0.36. Another material is MC-9 with an s23/s26 of less than 0.17 (not prior art). Yet another material is a prior-art material; it is a conventionally prepared commercial methylcellulose material (METHOCEL™ A15C methylcellulose, The Dow Chemical Company). The conventionally prepared material is not capable of gelling in water at body temperature at concentrations of 2 wt. % or less.

TABLE 3

Chemical structure and properties of methylcellulose materials

| Methylcellulose | DS (USP) | % methoxyl | mol fraction (26-Me) | mol faction (23-Me) | s23/s26 | gelation temperature $T_{gel}$ [° C.] | Viscosity η (5° C., 10 s$^{-1}$, 2 wt. %) [mPa·s] |
|---|---|---|---|---|---|---|---|
| A15C | 1.82 | 30.1 | 0.2617 ± 0.0012 | 0.1065 ± 0.0042 | 0.41 ± 0.02 | 48.0 | 2390 |
| MC-1 | 1.81 | 30.0 | 0.3029 ± 0.0016 | 0.0867 ± 0.0025 | 0.29 ± 0.01 | 40.7 | 1170 |
| MC-2 | 2.01 | 32.8 | 0.3000 ± 0.0024 | 0.0755 ± 0.0041 | 0.25 ± 0.01 | 37.7 | 923 |
| MC-3 | 2.01 | 32.8 | 0.3000 ± 0.0024 | 0.0755 ± 0.0041 | 0.25 ± 0.01 | 39.5 | 1870 |
| MC-4 | 2.01 | 32.8 | 0.3000 ± 0.0024 | 0.0755 ± 0.0041 | 0.25 ± 0.01 | 28.5 | 445 |
| MC-5 | 2.01 | 32.8 | 0.3000 ± 0.0024 | 0.0755 ± 0.0041 | 0.25 ± 0.01 | 39.0 | 1750 |
| MC-6 | 2.01 | 32.8 | 0.3000 ± 0.0024 | 0.0755 ± 0.0041 | 0.25 ± 0.01 | 36.7 | 1500 |
| MC-7 | 1.98 | 32.4 | 0.3202 ± 0.0004 | 0.0708 ± 0.0005 | 0.22 ± 0.00 | 31.7 | 730 |
| MC-8 | 1.98 | 32.4 | 0.3202 ± 0.0004 | 0.0708 ± 0.0005 | 0.22 ± 0.00 | 33.5 | 1630 |
| MC-9* | 1.80 | 29.8 | 0.3537 ± 0.0046 | 0.0564 ± 0.0050 | 0.16 ± 0.01 | 24.0 | 1136 |

*Comparative Example, but not prior art

The dependencies of the gel fracture force $F_{GF}$ (37° C.), gelation temperature and the viscosity on the type of methylcellulose and the level and type of mono- or disaccharides used in a set of aqueous formulations are summarized in Table 4. "MC wt. %, type" in Table 4 means the weight % and type of MC in the aqueous formulation, based on the total weight of the formulation. "Mono- or disaccharide wt. %, type" in Table 4 means the weight % of mono- and/or disaccharide in the aqueous formulation, based on the total weight of the formulation.

Example formulations of this invention are denoted as I-1, I-2, ... and I-19, while the comparative examples are denoted C-1, C-2. C-3, ... and C-16. Formulations C-1, C-2, and C-3 prepared with a prior art MC material (e.g. METHOCEL™ A15C methylcellulose, abbreviated as A15C) are fluid-like at 37° C. regardless of the level or type of mono- or disaccharides, and consequently their gel fracture force $F_{GF}$ (37° C.) values are zero. Values of $F_{GF}$ (37° C.) are elevated for the inventive examples (I-1, I-2, ... I-19) when a mono- and/or disaccharide is present. In Table 4 the mean values±the standard deviation 1σ of the gel fracture force $F_{GF}$ (37° C.) values of the aqueous solutions are listed.

Solution viscosities η (5° C., 10 s$^{-1}$) of the set of inventive and comparative examples are also summarized in Table 4. Note that the viscosities of the set of formulations with MC-1 to MC-8 used in the examples are not very sensitive to the presence of mono- and/or disaccharides in the formulation. Consequently, the mono- or disaccharide component provides an ability to enhance $F_{GF}$ (37° C.) with moderate impact to η (5° C., 10 s$^{-1}$).

TABLE 4

Dependencies of $F_{GF}$(37° C.), gelation temp. and viscosity on the level and type of methylcellulose and mono- and/or disaccharides used in the aqueous formulation

| (Comparative) Example | MC wt. %, type | s23/s26 | mono- or disaccharide wt. %, type | $F_{GF}$(37° C.) [N] | Gelation Temp. [° C.] | Viscosity η (5° C., 10 s$^{-1}$) [mPa·s] |
|---|---|---|---|---|---|---|
| C-1 | 2%, A15C | 0.41 | 0% | 0.0 ± 0.0 | 48.0 | 2390 |
| C-2 | 2%, A15C | 0.41 | ~12%, Smoothie | 0.0 ± 0.0 | 38.7 | 11720 |
| C-3 | 2%, A15C | 0.41 | 15%, Fructose | 0.0 ± 0.0 | 45.7 | 4949 |
| C-4 | 2%, MC-1 | 0.29 | 0% | 0.9 ± 0.0 | 40.7 | 1170 |
| I-1 | 2%, MC-1 | 0.29 | ~12%, Smoothie | 4.6 ± 0.2 | 22.2 | 8477 |
| I-2 | 2%, MC-1 | 0.29 | 15%, Fructose | 4.1 ± 0.3 | 27.2 | 2817 |
| C-5 | 2%, MC-2 | 0.25 | 0% | 0.0 ± 0.0 | 37.7 | 923 |
| I-3 | 2%, MC-2 | 0.25 | ~12%, Smoothie | 2.3 ± 0.2 | 22.9 | 5315 |
| I-4 | 2%, MC-2 | 0.25 | 15%, Fructose | 3.2 ± 0.4 | 25.2 | 1798 |
| C-6 | 2%, MC-3 | 0.25 | 0% | 0.0 ± 0.0 | 39.5 | 1870 |
| I-5 | 2%, MC-3 | 0.25 | ~12%, Smoothie | 3.7 ± 0.8 | 25.0 | 8654 |
| C-7 | 2%, MC-4 | 0.25 | 0% | 0.4 ± 0.1 | 28.5 | 445 |
| I-6 | 2%, MC-4 | 0.25 | 12.5%, Fructose | 2.4 ± 0.2 | 24.5 | 926 |
| I-7 | 2%, MC-4 | 0.25 | 15%, Fructose | 2.8 ± 0.2 | 22.0 | 1250 |
| I-8 | 2%, MC-4 | 0.25 | 17.5%, Fructose | 2.0 ± 0.3 | 22.0 | 1464 |
| C-8 | 2%, MC-5 | 0.25 | 0% | 0.9 ± 0.1 | 39.0 | 1750 |
| I-9 | 2%, MC-5 | 0.25 | 12.5%, Fructose | 3.5 ± 0.8 | 29.0 | 3654 |
| I-10 | 2%, MC-5 | 0.25 | 15%, Fructose | 4.2 ± 0.9 | 27.5 | 4189 |
| I-11 | 2%, MC-5 | 0.25 | 17.5%, Fructose | 4.1 ± 0.5 | 26.0 | 4135 |
| I-12 | 2%, MC-5 | 0.25 | 12.5%, Glucose | 3.5 ± 0.6 | 29.5 | 2760 |
| I-13 | 2%, MC-5 | 0.25 | 15%, Glucose | 4.3 ± 0.9 | 27.2 | 3193 |
| I-14 | 2%, MC-5 | 0.25 | 17.5%, Glucose | 6.3 ± 1.2 | 25.5 | 3720 |
| C-9 | 2%, MC-6 | 0.25 | 0% | 0.9 ± 0.1 | 36.7 | 1500 |
| I-15 | 2%, MC-6 | 0.25 | 12.5%, Saccharose | 3.5 ± 0.5 | 29.7 | 2472 |
| I-16 | 2%, MC-6 | 0.25 | 15%, Saccharose | 3.6 ± 0.7 | 28.5 | 2928 |
| I-17 | 2%, MC-6 | 0.25 | 17.5%, Saccharose | 3.5 ± 0.6 | 27.2 | 3329 |
| C-10 | 2%, MC-7 | 0.22 | 0% | 0.6 ± 0.1 | 31.7 | 730 |
| I-18 | 2%, MC-7 | 0.22 | 15%, Fructose | 1.4 ± 0.1 | 19.0 | 1220 |
| C-11 | 2%, MC-8 | 0.22 | 0% | 0.9 ± 0.2 | 33.5 | 1630 |
| I-19 | 2%, MC-8 | 0.22 | 15%, Fructose | 2.0 ± 0.2 | 23.7 | 2012 |

TABLE 4-continued

Dependencies of $F_{GF}(37°$ C.), gelation temp. and viscosity on the level and type of methylcellulose and mono- and/or disaccharides used in the aqueous formulation

| (Comparative) Example | MC wt. %, type | s23/s26 | mono- or disaccharide wt. %, type | $F_{GF}(37°$ C.) [N] | Gelation Temp. [° C.] | Viscosity η (5° C., 10 s$^{-1}$) [mPa · s] |
|---|---|---|---|---|---|---|
| C-12 | 2%, MC-9 | 0.16 | 0% | 2.1 ± 0.2 | 24.0 | 1136 |
| C-13 | 2%, MC-9 | 0.16 | ~12%, Smoothie | 0.0 ± 0.0 | n.a.* | 987 |
| C-14 | 2%, MC-9 | 0.16 | 15%, Fructose | 0.0 ± 0.0 | n.a.* | 88 |
| C-15 | — | — | ~12%, Smoothie | 0.0 ± 0.0 | n.a.* | 196 |
| C-16 | — | — | 17.5%, Fructose | 0.0 ± 0.0 | n.a.* | 4 |

*not analyzable; no analysis of the gelation temperature could be performed since the solution did not form gels at elevated temperatures When a mono- or disaccharide and a conventionally produced methylcellulose, which is commercially available from The Dow Chemical Company under the Trademark METHOCEL A15C, are used in combination, a viscosity increase of the solution at 5° C. results which is comparable to the viscosity increase that results from the combination of a mono- or disaccharide and methylcellulose having an s23/s26 of from 0.17 to 0.36.

A significant increase in gel fracture force $F_{GF}$ (37° C.) results when a mono- or disaccharide and methylcellulose having an s23/s26 of from 0.17 to 0.36 are combined in an aqueous formulation. In contrast, no increase in gel fracture force $F_{GF}$ (37° C.) results when a mono- or disaccharide and METHOCEL A15C methylcellulose are used in combination. Moreover, if a mono- or disaccharide and 2% of a methylcellulose having an s23/s26 of less than 0.17 (comparative methylcellulose MC-10) are used in combination in an aqueous solution, no gel fracture force $F_{GF}$ (37° C.) is measurable, although a 2% aqueous solution of comparative methylcellulose MC-10 alone has a measurable gel fracture force $F_{GF}$ (37° C.).

Production of Methylcellulose 10 (MC-10)

Methylcellulose 10 (MC-10) is produced according to the following procedure. Finely ground wood cellulose pulp is loaded into a jacketed, agitated reactor. The reactor is evacuated and purged with nitrogen to remove oxygen, and then evacuated again. The reaction is carried out in two stages. In the first stage, a 50 weight percent aqueous solution of sodium hydroxide is sprayed onto the cellulose until the level reaches 1.8 mol of sodium hydroxide per mol of anhydroglucose units of the cellulose, and then the temperature is adjusted to 40° C. After stirring the mixture of aqueous sodium hydroxide solution and cellulose for about 20 minutes at 40° C., 1.5 mol of dimethyl ether and 2.3 mol of methyl chloride per mol of anhydroglucose units are added to the reactor. The contents of the reactor are then heated in 60 min to 80° C. After having reached 80° C., the first stage reaction is allowed to proceed for 5 min. Then the reaction is cooled down to 65° C. in 20 min.

The second stage of the reaction is started by addition of methyl chloride in an amount of 3.4 mol equivalents of methyl chloride per mol of anhydroglucose unit. The addition time for methyl chloride is 20 min. Then a 50 weight percent aqueous solution of sodium hydroxide at an amount of 2.9 mol of sodium hydroxide per mol of anhydroglucose units is added over a time period of 45 min. The rate of addition is 0.064 mol of sodium hydroxide per mol of anhydroglucose units per minute. After the second-stage addition is completed the contents of the reactor are heated up to 80° C. in 20 min and then kept at a temperature of 80° C. for 120 min.

After the reaction, the reactor is vented and cooled down to about 50° C. The contents of the reactor are removed and transferred to a tank containing hot water. The crude methylcellulose is then neutralized with formic acid and washed chloride free with hot water (assessed by $AgNO_3$ flocculation test), cooled to room temperature and dried at 55° C. in an air-swept drier. The material is then ground using an Alpine UPZ mill using a 0.5-mm screen.

Key chemical structural parameters and properties of two methylcellulose materials are listed in Table 5 below. The mean values±the standard deviation 2σ of the mol fraction (26-Me), the mol fraction (23-Me) and s23/s26 are listed.

One material is methylcellulose 10 (MC-10) with an s23/s26 ratio from 0.17 to 0.36. The other material is a prior-art material; it is a conventionally prepared commercial methylcellulose material (METHOCEL™ A4M methylcellulose, The Dow Chemical Company). The conventionally prepared material is not capable of gelling in water at body temperature at concentrations of 2 wt. % or less.

TABLE 5

Chemical structure and properties of two methylcellulose materials

| Measurement | Methylcellulose 10 (MC-10) | METHOCEL™ A4M(A4M) |
|---|---|---|
| DS (USP) | 1.88 | 1.83 |
| % methoxyl | 30.9 | 30.3 |
| mol fraction (26-Me) | 0.3276 ± 0.0039 | 0.2615 ± 0.0026 |
| mol fraction (23-Me) | 0.0642 ± 0.0060 | 0.1017 ± 0.0056 |
| s23/s26 | 0.20 ± 0.02 | 0.39 ± 0.02 |
| Viscosity η (5° C., 10 s$^{-1}$, 2 wt. %) [mPa · s] | 5473 | 4620 |
| gelation temperature $T_{gel}$ [° C.] | 28 | 56 |

Qualitative Agreement Between In Vitro and In Vivo Metrics of Gels at 37° C.

MC-10 capable of gelling in water at 37° C. was used for the in vitro and in vivo metrics of gelation. A set of aqueous MC solutions was prepared similarly to that detailed in the "Production of a 2% aqueous solution of the methylcellulose" section, but (1) prepared at more dilute concentrations, (2) solutions were not stirred in an ice bath for 15 min prior to use and (3) the MC concentrations are reported in an alternative format (0.70, 0.90, 1.10, 1.30, 1.50 and 1.70% weight/volume).

Quantitative data for two in vitro experiments on this set of materials are listed in Table 6. The viscosity η (5° C., 10 s$^{-1}$) of the aqueous solutions are observed to increase as the MC concentration rises. Similarly, after these solutions are warmed to 37° C. and allowed sufficient time to gel, the fracture force $F_{GF}$ (37° C.) of the gels are also found to increase as the MC concentration rises.

Qualitative data for two in vivo experiments on this set of aqueous MC materials may also be found in Table 6. About 1.2 mL of each solution (about 7.5 mL/kg of body weight) was fed by gavage in to a set of fasting rats. Each rat had been fasting (water provided ad libitum) for 16 hours prior to the gavage step. About 45 minutes were allowed for the solution to gel as it warms to the rat body temperature. A set of three rats were sacrificed and dissected to observe the stomach contents. The stomach contents were observed visually for (1) the presence of gels, (2) the range of gel sizes, and (3) the gel modulus. The modulus of each gel was estimated with small mechanical deformations (e.g. with a spatula). The gel resistance to the deformation was used qualitatively to label the gel as either "soft" or "firm". The "No gel" observation in Table 6 indicates only a liquid flowed from the stomach. "Small soft gel" observation indicates the presence of small soft non-flowing gel masses surrounded by a liquid. "Large firm gel" observation indicates the presence of larger firmer non-flowing gel masses were present.

TABLE 6

Dependencies of the in-vitro gel fracture force and in-vivo observations of rat stomach contents on MC concentration after MC-10 was allowed to gel at 37° C.

| MC-10 Concentration [% wt/vol] | Solution Viscosity $\eta$(5° C., 10 s$^{-1}$) [mPa·s] | $F_{GF}$ (37° C.) [N] | Rat Stomach Content (in vivo) |
| --- | --- | --- | --- |
| 0.7% wt/vol | Not determined | No measurable gel | No gel |
| 0.9% wt/vol | Not determined | No measurable gel | Small soft gel |
| 1.1% wt/vol | 750 | 0.5 | Small soft gel |
| 1.3% wt/vol | 1300 | 1.1 | Small soft gel |
| 1.5% wt/vol | 2000 | 1.5 | Large firm gel |
| 1.7% wt/vol | 3000 | 2.4 | Stomach-shaped gel |

Interestingly, the 1.7% MC solution developed a gel mass that substantially filled the rat's stomach. Moreover, the gel mass maintained the shape of the rat's stomach after being removed from the stomach tissue and cooled to room temperature.

The results in Table 6 show a clear correlation between the gel fracture force in vitro of MC-10, having an s23/s26 of from 0.17 to 0.36, and stomach content in vivo.

Satiety

A human clinical study was commissioned to determine if methylcellulose 10 (MC-10) had a statistically-significant effect on satiety relative to prior-art methylcellulose. The study design was reviewed by a certified Institutional Review Board, and was conducted in accordance with International Conference on Harmonization/Good Clinical Practice standards.

Human satiety trials results are known to be affected by taste perceptions. Mint chocolate flavored formulations were prepared in order to make the samples palatable. Comparative Batch Z, a conventional commercially-available methylcellulose (METHOCEL™ A4M, The Dow Chemical Company), which had the properties as listed in Table 5 above, was selected to have a closely-matched solution viscosity with methylcellulose 10. A set of three aqueous formulations were studied and labeled either Batch X, Z or 1. The formulation components and levels of these batches are summarized in Table 7.

TABLE 7

Three key formulations used to probe satiety in human clinical studies.

| Component | Comparative Batch X | Comparative Batch Z | Batch 1 with Methylcellulose 10 |
| --- | --- | --- | --- |
| Xanthan, % [wt/wt] | 0.1 | — | — |
| METHOCEL A4M methylcellulose, % [wt/wt] | — | 2.0 | — |
| Methylcellulose 10, % wt/wt] | — | — | 2.0 |
| Cocoa, %, [wt/wt] | 2.0 | 2.0 | 2.0 |
| Sweetener, % [wt/wt] | 0.24 | 0.24 | 0.24 |
| Mint Oil, % [wt/wt] | 0.017 | 0.017 | 0.017 |
| Water, % [wt/wt] | 97.65 | 95.75 | 95.75 |

These aqueous flavored solutions were estimated to have a caloric content of less than 5 kcal for each 300-mL dose provided to the human participants. The caloric content is thought to arise solely from the flavorings and sweetener.

Four groups of human participants were created; each group would receive 300-mL dose of Batch X or 300-mL dose of Batch Z or 300-mL dose of Batch 1 or 150-mL dose of Batch 1. For the two control batches (X and Z), a 25-kg aqueous stock solution was prepared, and ultimately subdivided into 450-mL size pots (300 g/pot) directly after cooling and storage overnight at 3° C. The pot samples were frozen and stored at −20° C. prior to use. The frozen samples were removed from the freezer and defrosted at 7° C. for 24 h prior to consumption in the human trials.

For the test batch (1), a 30-kg aqueous stock solution was prepared. The batch was filled into 4-L plastic containers (2.4 kg per container), and the containers were rotated slowly overnight at 3° C. on a conveyer belt to degas the samples and to ensure full hydration of the methylcellulose component. The plastic containers were then frozen and stored at −20° C. Prior to consumption, a 2.4-kg sample in a 4 L container was defrosted, and used to provide the human participants with either a 300-mL or 150-mL dose. The sample was defrosted with a two-step process over two nights: (1) rotating at 7° C. for 28 h, and (2) rotating at 3° C. for 16 h.

A population of 32 participants was recruited according to the following seven criteria: (1) age at start of the study must be between or equal to 20 and 60 years old; (2) Body Mass Index (BMI) between or equal to 18.5 and 25 kg/m$^2$; (3) apparently healthy (as measured by questionnaire, no reported current or previous metabolic diseases or chronic gastrointestinal disorders); (4) good reported dietary habits (no medically prescribed diet, no slimming diet, accustomed to eating 3 meals a day); (5) no blood donation during the study; (6) less than or equal to ten hours per week of exercise/sporting activities; and (7) less than or equal to 21 (female) or 28 (male) alcoholic beverages a week. Additionally, potential participants were excluded for numerous issues (smoking, allergies or lactose intolerance, dislike, allergy or intolerance to experimental products, possible eating disorder (measured by SCOFF questionnaire), reported lactating (or lactating <6 weeks ago), pregnant (or pregnant <3 months ago) or wish to become pregnant during the study, reported medical treatment that might affect eating habits/satiety, or reported participation in another biomedical trial 1 month or less before the start of the study) that could complicate interpretation of the human trial data.

The four options (three solution types at 300-mL doses, and one solution type at 150-mL doses) were tested using a William's-squared randomized double-blind cross-over design. Over a period of four weeks, each participant visited the test facility on four occasions (each a "study day") to complete the study with one week wash-out period between each study day.

Participants were asked to eat as normal on the evening before the study day, but to stop eating at 20.00 hours, and to record everything they consumed between 18.00 and 20.00 hours. Drinking after 20.00 hours was allowed, but restricted only to water or tea/coffee with no sugar and no milk. Participants were also asked to abstain from alcohol and vigorous exercise for 24 hours prior to each study day, and to refrain from drinking any liquids for one hour before the start of the study day.

Participants were instructed to arrive at 08.45 hours on each study day. Participants completed baseline ratings for satiety feelings ten minutes before consumption of breakfast. A breakfast standardized for each participant's weight was provided consisting of cornflakes (0.67 g/kg) and semi-skimmed milk (2.5 g/kg) at 09.00 hours. Participants were seated in booths to isolate them and were instructed not to talk to each other. Participants were given 15 minutes to eat the breakfast Immediately post consumption, questionnaires on satiety were completed, after which the participants were free to leave the booths.

Questions on satiety were asked every 30 minutes until immediately prior consumption of the assigned batch sample. Thereafter, they received the assigned batch sample and were given fifteen minutes to consume it Immediately post consumption, questionnaires on satiety and liking were completed.

Non-caloric drinks (water, tea/coffee without milk/sugar) were allowed during the study day (however the participants were asked to abstain from drinking for 45 minutes before and after consumption of the assigned batch sample). To ensure similar conditions existed during each test day, mode of transportation and consumption of drinks (water, coffee/tea without milk/sugar) before and during the first test were recorded and repeated at each subsequent test.

Questions on satiety were then asked on a regular basis post consumption until immediately prior to consumption of an ad-libitum meal of a tomato and mozzarella pasta bake. Participants were given 30 minutes to consume the lunch and were instructed to eat only until they were comfortably full Immediately post consumption of the lunch, questionnaires on satiety and liking were completed. Energy consumed at the meal was measured by a determination of the mass of food eaten.

Multiple questions relating to satiety were asked of the participants, and responses were scored and entered, at least every 30 minutes, before and after breakfast consumption, before and after consumption of the assigned batch sample, before and after an ad-libitum meal. Statistical analysis was applied to the scores and a p value of lower than 0.05 was considered to be significant.

The four options (300 mL Batch X, 300 mL Batch Z, 300 mL Batch 1, and 150 mL Batch 1) received comparable responses for their smell, taste, texture, and overall comments, and thus differences in perceptions of hunger or fullness (discussed below) were not affected by the participants opinion of the sample itself.

Both Comparative Batch Z and inventive 300-mL Batch 1 received statistically significantly different responses, as compared to Comparative Batch X, to the questions "how hungry do you feel?," and "how full do you feel?," after consumption of the assigned batch sample until the ad-libitum meal 120 minutes later. In other words, the participants receiving Comparative Batch Z and inventive 300-mL Batch 1 felt less hungry over 120 minutes, and felt fuller for a more prolonged period of time. However, surprisingly in view of the similar responses, only the inventive Batch 1 at the 300-mL dosage displayed a statistically significant reduction of energy intake at the ad-libitum meal. Approximately 115-kcal reduction was achieved by consuming inventive Batch 1 at the 300-mL dosage; the result is equivalent to a 13% reduction of energy intake at the meal following consumption of the assigned batch sample.

Gelling in the Human Stomach

To demonstrate gelling and clearance of methylcellulose 10 (MC-10) in the stomachs of human volunteers, a clinical study using Magnetic Resonance Imaging (MRI) was performed. The study design was reviewed by a certified Institutional Review Board and was conducted in accordance with International Conference on Harmonization/Good Clinical Practice standards.

Comparative Batches M and N were a conventional, commercially available methylcellulose (METHOCEL A4M methylcellulose) and a blend of commercially available methylcelluloses (55% METHOCEL SGA16M methylcellulose and 45% METHOCEL SGA7C methylcellulose) respectively selected to have closely-matching initial solution viscosities with methylcellulose 10 (MC-10) used in the present invention. The DS(methyl) of the sample of METHOCEL SGA16M methylcellulose was 1.95; the DS(methyl) of the sample of METHOCEL SGA7C methylcellulose was 1.92. The levels of each formulation component reported in Table 8 are in weight percent.

TABLE 8

Three key formulations used to probe gelation in human stomaches.

| Component | Comparative Batch M | Comparative Batch N | Batch 2 with Methyl-cellulose 10 |
|---|---|---|---|
| METHOCEL A4M methylcellulose, % [wt/wt] | 2.0 | — | — |
| 55% METHOCEL SGA16M methylcellulose and 45% METHOCEL SGA7C methylcellulose, % [wt/wt] | — | 2.0 | — |
| Methylcellulose 10 (MC-10), % [wt/wt] | — | — | 2.0 |
| Caramel, % [wt/wt] | 0.25 | 0.25 | 0.25 |
| Sweetener (Sucofin, contains Maltodextrin and Aspartam), % [wt/wt] | 0.5 | 0.5 | 0.5 |
| Mint Oil, % [wt/wt] | 1 drop/ 650 ml | 1 drop/ 650 ml | 1 drop/ 650 ml |
| Water, % [wt/wt] | 97.24 | 97.24 | 97.24 |

$T_{gel}$ for METHOCEL A4M methylcellulose is 55° C.
$T_{gel}$ for METHOCEL SGA16M methylcellulose and METHOCEL SGA7C methylcellulose are each 38-44° C.
$T_{gel}$ for methylcellulose 10 (having an s23/s26 from 0.17 to 0.36) is 28° C.

For Batch 2, a 650-mL solution was made by adding the methylcellulose 10 (MC-10) to water at room temperature with stirring at 500 rpm (IKA—overhead stirrer—propeller), then cooling to about 2.5° C. for 6 hours (the speed of the stirrer was reduced stepwise: 500 rpm for 15 min, then 400 rpm for 10 min, then 200 rpm for 10 min, and then 100 rpm for 5 h). Flavors were added with stirring at about 700 rpm with lab stirrer system (IKA Eurostar 6000 with propeller) in a ice-water bath, and stored without stirring in a refrigerator at about 0-2° C. overnight to de-gas.

For Comparative Batches M and N, the 650-mL solutions were made by adding the methylcellulose to stirring water at 40-50° C. at 800 rpm (IKA—overhead stirrer—propeller), then stirring at 500 rpm for 15 min, cooling to about 2.5° C. for 90 min. Flavors were added with stirring at about 700 rpm with lab stirrer system (IKA Eurostar 6000 with propeller) in an ice-water bath, and stored in a refrigerator at about 0-2° C. overnight to de-gas. Samples were weighed into 300-mL aliquots and kept frozen prior to use.

In a 3-way randomized double-blind crossover study, six participants attended on three different occasions scheduled approximately one week apart. MRI data were acquired with a 3T Philips Achieva MRI scanner. A range of MRI sequences ($T_1$ and $T_2$ weighted and $T_2$ mapping) was used. Each volunteer was positioned supine in the scanner with a SENSE body coil wrapped up around the abdomen. Multislice, $T_2$-weighted axial images of the gastric contents were acquired at selected time intervals; similarly single-slice quantitative $T_2$ mapping of the gastric contents was acquired. Each image set is acquired on a short hold of the participant's breath. Commercial software (Analyze 6, Biomedical Imaging Resources, Mayo Clinic, Rochester, Minn.) was used to trace manually around the region of interest on each slice. Volumes and $T_2$ values were calculated, and used to track formation and clearance of the gel from the stomach.

Participants were initially scanned at fasting to ensure the stomach was empty. They were then fed one of the three options (Comparative Batch M, Comparative Batch N or Batch 2 with MC-10). The participants were then imaged at intervals for up to four hours to study the dynamics of gel formation. A 500-mL water refill drink was given once the stomach appeared empty, and a final scan was taken to assess gel retention. Batch 2 was observed to gel in vivo. Comparative Batch M and N were observed to not gel.

The combined set of in-vitro and in-vivo studies of aqueous MC materials emphasize the ability of MC-10 materials (having an s23/s26 from 0.17 to 0.36) to form gel masses in the stomach when warmed to normal body temperatures (about 37° C.) of many mammals, including mice, hamsters, and humans, and to induce satiety. It is similarly expected that aqueous formulations, that contain an additional component (e.g. mono-, di- and/or oligosaccharides), will also induce satiety when their gel fracture forces $F_{GF}$ (37° C.) are comparable or exceed a critical value (typically about 2 N).

The invention claimed is:

1. A flowable or spoonable medicament, food, food ingredient or food supplement comprising (a) one or more mono-, di- and/or oligosaccharides and (b) a methylcellulose, wherein the methylcellulose has anhydroglucose units joined by 1-4 linkages wherein hydroxy groups of anhydroglucose units are substituted with methyl groups such that s23/s26 is from 0.17 to 0.36,
   wherein s23 is the molar fraction of anhydroglucose units wherein only the two hydroxy groups in the 2- and 3-positions of the anhydroglucose unit are substituted with methyl groups and
   wherein s26 is the molar fraction of anhydroglucose units wherein only the two hydroxy groups in the 2- and 6-positions of the anhydroglucose unit are substituted with methyl groups
   wherein the methylcellulose has a viscosity of from 200 to 10,000 mPa·s, measured as 2 wt. % aqueous solution at 5° C. at a shear rate of 10 s$^{-1}$, and
   wherein the weight ratio of (a) the total of one or more mono-, di- and/or oligosaccharides and (b) the methylcellulose is from 2.0:1.0 to 20:1.0.

2. The medicament, food, food ingredient or food supplement of claim 1, wherein the methylcellulose has a DS(methyl) of from 1.55 to 2.25.

3. The medicament, food, food ingredient or food supplement of claim 1, wherein the methylcellulose has a viscosity of from 400 to 7000 mPa·s, measured as 2 wt. % aqueous solution at 5° C. at a shear rate of 10 s$^{-1}$.

4. The medicament, food, food ingredient or food supplement of claim 1, wherein the weight ratio of (a) the total of one or more mono-, di- and/or oligosaccharides and (b) the methylcellulose is from 5.0:1.0 to 15:1.0.

5. The medicament, food, food ingredient or food supplement of claim 1, wherein the medicament, food, food ingredient or food supplement is useful for indications that require gastric volume to be occupied for at least 60 minutes.

6. The medicament, food, food ingredient or food supplement of claim 1, that when ingested by an individual, forms a gel mass in the individual's stomach.

7. The medicament, food, food ingredient or food supplement of claim 1, wherein the medicament, food, food ingredient or food supplement additionally comprises an aqueous liquid and the amount of the methylcellulose is from 0.5 to 2.5 weight percent, based on the total weight of the liquid composition.

8. The medicament, food, food ingredient or food supplement of claim 1 being in powder or granular form designed to be mixed with an aqueous liquid before consumption.

9. The food, food ingredient or food supplement of claim 1, wherein the food, food ingredient or food supplement is useful as a slimming aid, weight loss aid, or weight control aid in a non-obese individual.

10. The medicament of claim 1, wherein the medicament is useful for treating gastric ulcers, gastro-esophageal reflux disease, or obesity.

11. A method for inducing satiety or for reversibly reducing stomach void volume in an individual, comprising administering to said individual the medicament, food, food ingredient or food supplement of claim 1.

12. A method of reducing caloric intake in an individual, comprising administering to said individual the medicament, food, food ingredient or food supplement of claim 1.

13. The method of claim 11, wherein the medicament, food, food ingredient or food supplement is administered at least 45 minutes before the individual eats.

14. The method of claim 11, wherein the individual is obese.

15. The method of claim 11, wherein the individual is not obese.

16. The method of claim 12, wherein the medicament, food, food ingredient or food supplement is administered at least 45 minutes before the individual eats.

17. The method of claim 12, wherein the individual is obese.

18. The method of claim 12, wherein the individual is not obese.

19. The medicament, food, food ingredient or food supplement of claim 1, wherein said one or more mono-, di- and/or oligosaccharides are selected from the group consisting of mono- and disaccharides.

* * * * *